United States Patent [19]

Wu

[11] 4,279,637
[45] Jul. 21, 1981

[54] HERBICIDAL N-SUBSTITUTED 4-IMIDAZOLIN-2-ONES

[75] Inventor: Frank Wu, Libertyville, Ill.

[73] Assignee: Velsicol Chemical Corporation, Chicago, Ill.

[21] Appl. No.: 154,185

[22] Filed: May 29, 1980

Related U.S. Application Data

[63] Continuation-in-part of Ser. No. 52,525, Jun. 2, 1979, abandoned.

[51] Int. Cl.³ .................... A01N 43/50; C07D 233/70
[52] U.S. Cl. ........................................ 71/92; 548/319; 548/322; 560/9; 560/12; 560/27; 564/48; 564/49; 564/50; 564/51; 564/52; 564/53; 564/54; 564/315; 564/430
[58] Field of Search ..................... 548/319, 322; 71/92

[56] References Cited

U.S. PATENT DOCUMENTS

| | | | |
|---|---|---|---|
| 3,119,682 | 1/1964 | Martin et al. | 71/92 X |
| 3,133,079 | 5/1964 | Luckenbaugh | 71/92 X |
| 3,216,816 | 11/1965 | Luckenbaugh | 71/92 |
| 3,303,199 | 2/1967 | Doebel et al. | 424/273 R X |
| 3,303,199 | 2/1967 | Doebel et al. | 424/273 R X |
| 3,459,757 | 8/1969 | Wright et al. | 424/266 X |
| 3,459,757 | 8/1969 | Wright et al. | 424/266 X |
| 3,579,500 | 5/1971 | Jelinek | 71/92 X |
| 3,933,839 | 1/1976 | Krenzer | 71/90 X |
| 3,944,409 | 3/1976 | Krenzer | 71/90 |
| 3,990,882 | 11/1976 | Krenzer | 71/90 |
| 4,093,446 | 6/1978 | Bayer et al. | 71/92 X |

Primary Examiner—Richard A. Schwartz
Attorney, Agent, or Firm—Dietmar H. Olesch; Robert J. Schwarz

[57] ABSTRACT

This invention discloses chemical compounds of the formula

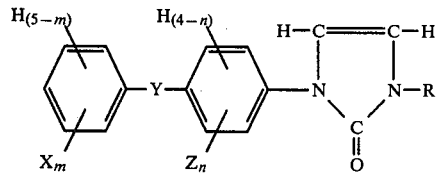

wherein X and Z are each independently selected from the group consisting of halogen, haloalkyl, nitro, cyano, alkyl, alkoxy and alkylthio; m and n are each independently integers of from 0 to 4; Y is selected from the group consisting of oxygen, sulfur, methylene, sulfonyl and sulfinyl; and R is selected from the group consisting of hydrogen, alkyl and alkoxy. The compounds of the above description are useful as herbicides.

10 Claims, No Drawings

HERBICIDAL N-SUBSTITUTED 4-IMIDAZOLIN-2-ONES

This application is a continuation-in-part of application, Ser. No. 52,525 filed June 2, 1979, now abandoned.

this invention relates to new compositions of matter and more particularly relates to new chemical compounds of the formula

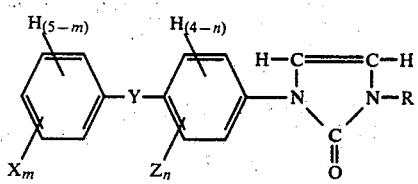

wherein X and Z are each independently selected from the group consisting of halogen, haloalkyl, nitro, cyano, alkyl, alkoxy and alkylthio; m and n are each independently integers of from 0 to 4; Y is selected from the group consisting of oxygen, sulfur, methylene, sulfonyl and sulfinyl; and R is selected from the group consisting of hydrogen, alkyl and alkoxy.

The compounds of this invention are useful as herbicides.

In a preferred embodiment of this invention, X and Z are each independently selected from the group consisting of halogen, lower haloalkyl, nitro, cyano, lower alkyl, lower alkoxy and lower alkylthio; m and n are each independently integers of from 0 to 4; Y is selected from the group consisting of oxygen, sulfur, methylene, sulfonyl and sulfinyl; and R is selected from the group consisting of hydrogen, lower alkyl and lower alkoxy. The term "lower" as used herein designates a straight or branched carbon chain of up to six carbon atoms.

The compounds of the present ivention can be prepared by heating a compound of formula

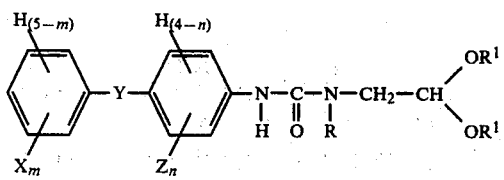

wherein X, Y, Z, R, m and n are as hereinbefore described and R¹ is alkyl, in a dilute, aqueous, acidic reaction medium for a period of from about 10 minutes to about 60 minutes. Temperatures of from about 70° C. to the reflux temperature of the mixture may be used. The reaction medium can comprise a dilute aqueous inorganic acid such as hydrochloric at a concentration of from about 0.5 to about 5 percent. Upon completion of the reaction, the desired product may be isolated and purified by conventional means such as evaporation of the reaction medium, extraction, crystallization and the like.

The compounds of formula II can be prepared by reacting approximately equimolar amounts of a compound of formula

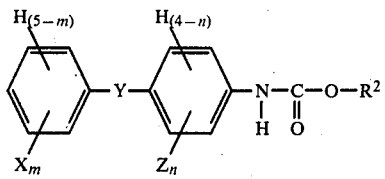

wherein X, Y, Z, m and n are as hereinbefore described and $R^2$ is methyl or ethyl with a compound of formula $$HN-CH_2-CH \diagup OR^1 \diagdown OR^1 \quad \text{IV}$$
$$\phantom{HN-CH_2-}|\phantom{CH}$$
$$\phantom{HN-CH_2-}R$$

wherein R and $R^1$ are as hereinbefore described. While any dialkylacetal of formula IV may be used, the diethyl or dimethyl acetal are preferred because of their ready commercial availability. The reaction may be effected by combining the compounds of formula III and IV in the presence of an inert reaction medium such as toluene or xylene and heating at from about 80° C. to about 120° C. for a period of from 2 hours to 16 hours. The product can be isolated and purified by techniques standard in the art.

The compounds of formula III can be prepared by reacting a compound of formula

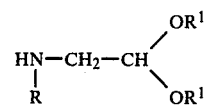

wherein X, Y, Z, m and n are as heretofore described, with the methyl or ethyl ester of chloroformic acid. This reaction can be effected by adding the chloroformate to a solution of the compound of formula V in the presence of an acid acceptor such as tertiary amine at a temperature of from about 0° C. to 50° C. The tertiary amine may itself serve as the solvent used to dissolve the compound of formula V. Pyridine, for example, may be used both as solvent and acid acceptor. A slight molar excess of chloroformate may be used to ensure completeness of the reaction. After addition of the chloroformate is completed, the reaction mixture can be stirred, at room temperature, for an additional period of from 2 hours to 16 hours to promote completeness of reaction. The desired product can be recovered and purified by standard techniques of the art.

The acetal of formula IV when not readily available can be prepared by reacting an amine of the formula $$H-N-H \quad \text{VI}$$
$$\phantom{H-}|$$
$$\phantom{H-N}R$$

wherein R is as heretofore described with the diethyl acetal of 2-bromoacetaldehyde. This reaction can be effected by combining from about 1 to 2 molar amounts of the amine of formula VI with one molar amount of the diethyl acetal of 2-bromoacetaldehyde in about equimolar portions in an inert organic reaction medium such as methanol. The reaction mixture can then be heated at reflux for a period of from about 4 to about 8 hours. After this time the reaction mixture can be cooled to room temperature and an alkali metal hydroxide or carbonate can be added in an amount sufficient to neutralize the reaction mixture. Stirring can be continued at room temperature for a period of up to about 24 hours to ensure completion of the reaction. The desired product can be isolated and purified by standard techniques.

Exemplary compounds of formula V useful preparing the compound of the present invention are 4-(4-chlorophenoxy)benzenamine, 4-[-(trichloromethyl)phenoxy]-benzenamine, 4-[(2,3-dichlorophenyl)thio]-2-methylbenzenamine, 4-(4-ethylphenoxy)-benzenamine, 4-(2-propylphenoxy)-2-chlorobenzamine, 4-(4-methoxyphenoxy)benzenamine, 4-(4-methoxyphenoxy)-3-methoxybenzamine, 4-[2,3-(dimethoxyphenyl)methyl]-benzenamine, 4-[2,5-(dichlorophenyl)methyl]-5-bromobenzenamine, 4-[2,3,5-trimethoxyphenyl)sulfonyl]benzenamine, 4[(4-bromophenyl) sulfinyl]benzenamine, 4(phenoxyphenyl)-3-methoxybenzenamine, 4-3,4,5-trimethylphenoxy)-3,5-dimethylbenzenamine, 4-(5-propylphenoxy)-benzenamine, 4-(3-cyanophenoxy)-3-nitrobenzenamine, 4-[(2-nitrophenyl)sulfonyl]2-cyanobenzenamine, 4-[(2-cyanophenyl)sulfinyl]-3-(ethylthio)benzenamine, 4-(phenoxy)-2,6-diemthyl-3,5-dichlorobenzenamine.

The manner in which the compounds of the present invention can be prepared is more specifically illustrated in the following examples.

EXAMPLE 1

PREPARATION OF ETHYL (4-PHENOXYPHENYL)CARBAMATE

4-Phenoxybenzenamine (18.5 grams; 0.1 mole) and pyridine (50 ml) were charged into a glass reaction vessel fitted with a mechanical stirrer and thermometer and cooled to about 4° C. Ethyl chloroformate, (13.5 grams; 0.125 mole) was added and the reaction stirred at about 4° C. for a period of about 30 minutes, stirring was then continued at room temperature for another 16 hours. Crystallization occured, whereupon the precipitate was filtered from the reaction medium, washed with water, and air dried to give the desired product ethyl (4-phenoxyphenyl)carbamate.

EXAMPLE 2

PREPARATION OF N-(4-PHENOXYPHENYL)-N'-(2,2-DIEMTHOXYETHYL)-N'-METHYLUREA

Ethyl (4-phenoxyphenyl)carbamate (15.8 grams; 0.058 mole), N-(2,2-dimethoxyethyl)methanamine (16 grams; 0.14 mole) and toluene (100 ml) were charged into a glass reaction vessel equipped with a mechanical stirrer, thermometer and condenser. The mixture was refluxed for 16 hours. The solvent was then removed by mild warming under reduced pressure to yield the desired product N-(4-phenoxyphenyl)-N'-(2,2-diemthoxyethyl)-N'-methylurea as a solid having a melting point of 81° C.

EXAMPLE 3

PREPARATION OF 1METHYL-3-(4-PHENOXYPHENYL)-4-IMIDAZOLIN-2-ONE

N-(4-Phenoxyphenyl)-N'-(2,2-dimethoxyethyl)-N'-methylurea (5.0 grams, 0.015 mole), water (30 ml) and concentrated hydrochloric acid (3 ml) were charged into a glass reaction vessel fitted with a mechanical stirrer thermometer and condenser. The reaction mixture was refluxed for a period of about 15 minutes, cooled and extracted with ethyl acetate. The ethyl acetate solution was washed with dilute aqueous sodium bicarbonate and with portions of water and dried. The ethyl acetate was removed by mild warming under reduced pressure to yield a residue. This was recrystalized from ethyl acetate to yield the desired product 1-methyl-3-(4-phenoxyphenyl)-4-imidazolin-2-one as a solid having a melting point of 112° C.

EXAMPLE 4

PREPARATION OF ETHYL [4-(4-CHLOROPHENOXY)PHENYL]CARBAMATE 4-(4-Chlorophenoxy)benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., and then for an additional 16 hours at room temperature. The mixture is then washed with 2 portions of water (50 ml), dried and the solvent is then removed to yield the desired product ethyl [4-(4-chlorophenoxy)-phenyl]carbamate.

EXAMPLE 5

PREPARATION OF N-[4(4-CHLOROPHENOXY)PHENYL]-N'-(2,2-DIMETHOXYETHYL)-N'-METHYLUREA

Ethyl [4-(4-chlorophenoxy)phenyl]carbamate (0.1 mole) and toluene (100 ml) are charged into a glass vessel fitted with a mechanical stirrer, thermometer and condenser. N-(2,2-diemthoxyethyl)methanamine (0.15 mole) is added to the vessel and the mixture is refluxed for 16 hours. Solvent is then removed by mild warming under reduced pre-sure to yield the desired product N-[4-(4-chlorophenoxy)phenyl]-N-(2,2-dimethoxyethyl)-N-methylurea.

EXAMPLE 6

PREPARATION OF 1-METHYL-3-[4-(4-CHLOROPHENOXY)-PHENYL]-4-IMIDAZOLIN-2-ONE

N-[4-(4-Chlorophenoxy)phenyl]-N'-(2,2-dimethoxyethyl)-N'-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes and then cooled and extracted with ethyl acetate. The extract is washed with dilute aqueous sodium bicarbonate, with two portions of water, and dried. The ethyl acetate is removed by mild warming at reduced pressure to yield the desired product 1-methyl-3-[4-(4-chlorophenoxy)phenyl]-4-imidazolin-2-one.

EXAMPLE 7

PREPARATION OF ETHYL [4-(4-METHOXYPHENOXY)PHENYL]CARBAMATE 4-(4-Methoxyphenoxy)benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C., then for an additional 16 hours at room temperature. The mixture is then washed with 2 portions of water (50 ml), dried and the solvent is then removed to yield the desired product ethyl [4-(4-methoxyphenoxy)phenyl]carbamate.

EXAMPLE 8

PREPARATION OF N-[4-(4-METHOXYPHENOXY)PHENYL]-N'-(2,2-DIMETHOXYETHYL)-N'-METHYLUREA

Ethyl [4-(4-methoxyphenoxy)phenyl]carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4(4-methoxyphenoxy)phenyl]-N'-(2,2-dimethoxyethyl)-N'-methylurea.

EXAMPLE 9

PREPARATION OF 1-METHYL-3-[4-(4-METHOXYPHENOXY)-PHENYL]-4-IMIDAZOLIN-2-ONE

N-[4-(4-Methoxyphenoxy)phenyl]-N-(2,2-dimethoxyethyl)-N-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes and then cooled and extracted with ethyl acetate. The extract is washed with dilute aqueous solution bicarbonate, with two portions of water and is then dried. The ethyl acetate is removed by mild warming under reduced pressure to yield the desired product 1-methyl-3-[4-(4-methoxyphenoxy)-phenyl]-4-imidazolin-2-one.

EXAMPLE 10

PREPARATION OF ETHYL [4-(3,4-DICHLOROPHENOXY)PHENYL]CARBAMATE 4-(3,4-Dichlorophenoxy)benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-(3,4-dichlorophenoxy)phenyl]-carbamate.

EXAMPLE 11

PREPARATION OF N-[4-(3,4-DICHLOROPHENOXY)PHENYL]-N'-(2,2DIMETHOXETHYL)-N-METHYLUREA

Ethyl [4-(3,4-dichlorophenoxy)phenyl]carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4-(3,4-dichlorophenoxy)-phenyl]-N'-(2,2-dimethoxethyl)-N'-methylurea.

EXAMPLE 12

PREPARATION OF 1-METHYL-3-[4-(3,4-DICHLOROPHENOXY)-PHENYL]-4-IMIDAZOLIN-2-ONE.

N-[4-(3,4-Dichlorophenoxy)phenyl]-N'-(2,2-dimethoxyethyl)-N'-methylurea (0.02 mole), water (30 ml) and concentrated hydrochloric acid (3 ml) are changed into a glass reaction vessel fitted with a mechanical stirrer, thermometer and condenser. The mixture is refluxed for a period of about 30 minutes and then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3-[4-(3,4-dichlorophenoxy)phenyl]-4-imidazolin-2-one.

EXAMPLE 13

PREPARATION OF ETHYL [3,5-DICHLORO-4-(3,5-DICHLOROPHENOXY)-PHENYL]CARBAMATE.

3,5-Dichloro-4-(3,5-dichlorophenoxy)benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [3,5-dichloro-4-(3,5-dichlorophenoxy)phenyl]carbamate.

EXAMPLE 14

PREPARATION OF N-[3,5-DICHLORO-4-(3,5-DICHLOROPHENOXY)-PHENYL]-N'-(2,2-DIMETHOXYETHYL)-N'-METHYLUREA

Ethyl [3,5-dichloro-4-(3,5-dichlorophenoxy)phenyl]-carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[3,5-dichloro-4-(3,5-dichlorophenoxy)phenyl]-N'-(2,2-dimethoxyethyl)-N'-methylurea.

EXAMPLE 15

PREPARATION OF 1-METHYL-3-[3,5-DICHLORO-4-(3,5-DICHLOROPHENOXY)PHENYL]-4-IMIDAZOLIN-2-ONE.

Ethyl [3,5-dichloro-4-(3,5-dichlorophenoxy)phenyl]-carbamate (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes and then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3-[3,5-dichloro-4-(3,5-dichlorophenoxy) phenyl]-4-imidazolin-2-one.

EXAMPLE 16

PREPARATION OF ETHYL [4-(3,5-DINITROPHENOXY)PHENYL]CARBAMATE

[4-(3,5-Dinitrophenoxy)phenyl]benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-(3,5-dinitrophenoxy)phenyl]carbamate.

EXAMPLE 17

PREPARATION OF N-[4-(3,5-DINITROPHENOXY)PHENYL]-N'-(2,2-DIMETHOXYETHYL)-N'-METHYLUREA

Ethyl [4,(3,5-dinitrophenoxy)phenyl]carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4-(3,5-dinitrophenoxy)phenyl]-N'-(2,2-dimethoxyethyl)-N'-methylurea.

EXAMPLE 18

PREPARATION OF 1-METHYL-3-[4-(3,5-DINITROPHENOXY)-PHENYL]IMIDAZOLIN-2-ONE

N-[4-(3,5-Dinitrophenoxy)phenyl]-N'-(2,2-dimethoxyethyl)-N'-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes and then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3-[4-(3,5-dinitrophenoxy)-phenyl]-imidazolin-2-one.

EXAMPLE 19

PREPARATION OF ETHYL [4-[3-(TRIFLUOROMETHYL)PHENOXY]-PHENYL]CARBAMATE

4-[3-(trifluoromethyl)phenoxy]benzenamine (6.0 grams; 0.21 mol) and pyridine (50 ml) were placed in a glass reaction vessel equipped with a mechanical stirrer and placed in an ice bath. Ethyl chloroformate (5 ml) was added dropwise to the reaction mixture with continuous stirring. Stirring was continued overnight and the mixture was then poured into ice water (500 ml). The precipitate was washed with water and dried. It was found to have a melting point of 74°–75.5° C. In fraud analysis confirmed the identity of the desired product.

EXAMPLE 20

PREPARATION OF N-[4-[3-(TRIFLUOROMETHYL)PHENOXY]-PHENYL]-N'-(2,2-DIMETHOXYETHYL)-N'-METHYLUREA

Ethyl[4-[3-(trifluoromethyl)phenoxy]-phenyl]carbamate (7.1 grams; 0.02 mol) and N-(2,2-dimethoxyethyl) methanamine (15 ml) were charged into a glass reaction vessel equipped with mechanical stirrer, thermometer and reflux condenser. The mixture was refluxed for about 36 hours at a temperature of about 120° C. The product was recrystallized from ethyl acetate, then recrystallized from hexane giving the desired product having a melting point of 86°–88° C.

EXAMPLE 21

PREPARATION OF 1-METHYL-3-[4-[3-TRIFLUOROMETHYL)-PHENOXY]PHENYL]-4-IMIDAZOLIN-2-ONE

N-[4-[3-(Trifluoromethyl)phenoxy]phenyl]-N'-(2,2-dimethoxyethyl)-N'-methylurea (3.98 grams; 0.01 mol), ethylene glycol (0.53 grams; 0.01 mol) and paratoluenesulfonic acid (0.1 grams) in toluene (50 ml) were charged into a glass reaction vessel equipped with mechanical stirrer, thermometer and reflux condenser. The reaction mixture was heated gradually in an oil bath to a temperature of 100° C. overnight. The volatile materials were removed and the temperature was raised to 125° C. Additional distillate (10 ml) was collected. The toluene solvent was removed. The mixture was maintained with stirring overnight at 125° C. and an oily product recovered. This material was purified by liquid chromatography resulting in a white crystalline product (1.4 grams) having a melting point of 79°–84° C. Infraud analysis confirmed it to be the desired product. The following elemental analysis of this product was made:

| | C | H | N |
|---|---|---|---|
| Theoretical | 61.08 | 3.92 | 8.38 |
| Found | 60.79 | 4.14 | 8.20 |

EXAMPLE 22

PREPARATION OF ETHYL [4-(PHENYLMETHYL)PHENYL]CARBAMATE 3-(Phenylmethyl)benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portion of water (50 ml), dried and the solvent is then removed to yield the desired product ethyl [N-(phenylmethyl)phenyl]carbamate.

EXAMPLE 23

PREPARATION OF N-[4-(PHENYLMETHYL)PHENYL]-N'-(2,2-DIMETHOXYETHYL)-N'-METHYLUREA

Ethyl [4-(phenylmethyl)phenyl]carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4-(phenylmethyl)phenyl]-N'-(2,2-dimethoxyethyl)-N'-methylurea.

EXAMPLE 24

PREPARATION OF 1-METHYL-3-[4-(PHENYLMETHYL)PHENYL]-4-IMIDAZOLIN-2-ONE

N-[3-(Phenyl-methyl)phenyl]-N'-(2,2-dimethoxyethyl)-N'-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes and then cooled and extracted with ethyl acetate. The extract is washed with dulute aqueous sodium bicarbonate, with two portions of water and is then dried. The ethyl acetate is removed by mild warming under reduced pressure to yield the desired product 1-methyl-3-[4-(phenylmethyl)phenyl]-4-imidazolin-2-one.

EXAMPLE 25

PREPARATION OF ETHYL [4-[(2,3,5,6-TETRACHLOROPHENYL)METHYL]-PHENYL]CARBAMATE

4-[2,3,5,6-Tetrachlorophenyl)methyl]benezenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-[(2,3,5,6-tetrachlorophenyl)methyl]phenyl]carbamate.

EXAMPLE 26

PREPARATION OF N-[4-[(2,3,5,6-TETRACHLOROPHENYL)METHYL]PHENYL]-N-(2,2-DIMETHOXYETHYL)-N-METHYLUREA

Ethyl [4-[(2,3,5,6-tetrachlorophenyl)methyl]phenyl]-carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4-[2,3,5,6-tetrachlorophenyl)methyl]phenyl]-N-(2,2-dimethoxyethyl)-N-methylurea.

EXAMPLE 27

PREPARATION OF 1-METHYL-3-[4-[(2,3,5,6-TETRACHLOROPHENYL)METHYL]PHENYL]-4-IMIDAZOLIN-2-ONE

N-[4-[(2,3,5,6-Tetrachlorophenyl)methyl]phenyl]-N-(2,2-dimethoxyethyl)-N-methylurea (0.02 mole), water (30 ml) and concentrated hydrochloric acid, (3 ml) are charged into a glass reaction vessel fitted with a mechanical stirrer, thermometer and condenser. The mixture is refluxed for a period of about 30 minutes and then cooled and extracted with ethyl acetate. The extract is washed with dilute aqueous sodium bicarbonate, with two portions of water and is then dried. The ethyl acetate is removed by mild warming under reduced

EXAMPLE 28

ETHYL [4-[4-(METHOXYPHENYL)THIO]PHENYL]CARBAMATE

4-[4-Methoxyphenyl)thio]benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-[4-(methoxyphenyl)thio]phenyl]carbamate.

EXAMPLE 29

PREPARATION OF N-[4-[4-(METHOXYPHENYL)THIO]PHENYL]-N'-(2,2-DIEMTHOXYETHYL)-N'-METHYLUREA

Ethyl [4-[4-(methoxyphenyl)thio]phenyl]carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4-[4-(methoxyphenyl)thio]phenyl]-N'-(2,2-dimethyl)-N'-methylurea.

EXAMPLE 30

PREPARATION OF 1-METHYL-3-[4-[4-(METHOXYPHENYL)THIO]-PHENYL]-4-IMIDAZOLIN-2-ONE

N-[4-[4-Methoxyphenyl)thio]phenyl]-N'-(2,2-dimethoxyethyl)-N'-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes and then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3-[4-[4-(methoxyphenyl)thio]phenyl]-4-imidazolin-2-one.

EXAMPLE 31

PREPARATION OF ETHYL [3-METHOXY-4-(4-CHLOROPHENOXY)-PHENYL]CARBAMATE

3-Methoxy-4-[3-(4-chlorophenoxy)]benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [3-methoxy-4-[(3-methoxyphenyl)sulfinyl]phenyl]carbamate.

EXAMPLE 32

PREPARATION OF N-[3-METHOXY-4-[(4-CHLOROPHENOXY)]-PHENYL]-N'-(2,2-DIMETHOXYETHYL)-N-METHYLUREA

Ethyl [4-(3-methoxy)-4-(4-chlorophenoxy)phenyl]-carbamate (0.01 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[3-methoxy-4-[(4-chlorophenoxy)]phenyl[-N'-(2,2-dimethoxyethyl)-N'-methylurea.

EXAMPLE 33

PREPARATION OF 1-METHYL-3-[4-(3-METHOXY-4-CHLORO-PHENOXY)PHENYL]-4-IMIDAZOLIN-2-ONE

N-[3-Methoxy-4-[(4-chlorophenoxy)]phenyl]-N'-(2,2-dimethoxyethyl)-N-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes and then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3-[4-(3-methoxy-4-chlorophenoxy)phenyl]-4-imidazolin-2-one.

EXAMPLE 34

PREPARATION OF ETHYL [3-CHLORO-4-(4-METHYLPHENOXY)PHENYL]-CARBAMATE

3-CHLORO-4-[3-4-(methylphenoxy)]benzenamine (0.01 mole) and pyridine (50 ml) are charged into a glass reaction vessel fitted with a mechanical stirrer and thermometer and are cooled to about 5° C. Ethyl chloroformate (0.125 mole) is added with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-[(2,3,4-trichlorophenyl)sulfonyl]phenyl]carbamate.

EXAMPLE 35

N-[3-CHLORO-4-[(4-METHYLPHENOXY)]-PHENYL]-N'-METHOXYETHYL)-N'-METHYLUREA

Ethyl [3-chloro-4-(4-methylphenoxy)]carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[3-chloro-4-[(4-methylphenoxy)]phenyl]-N'-(2,2-dimethoxyethyl)-N-methylurea.

EXAMPLE 36

PREPARATION OF 1-METHYL-3-[4-[3-(CHLORO-4-METHYL-PHENOXY)PHENYL]-4-IMIDAZOLIN-2-ONE

N-[3-chloro-4-[(4-methylphenoxy)]phenyl]-N'-(2,2-dimethoxyethyl)-N'-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes and then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3-[4-[3-chloro-4-methylphenoxy]phenyl]-4-imidazolin-2-one.

EXAMPLE 37

PREPARATION OF ETHYL [4-(3-PENTYLPHENOXY)-2,3,5,6-TETRAPEN-TYLPHENYL]CARBAMATE

[4-(3-Pentylphenoxy)-3-pentylphenyl]benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-(3-pentylphenoxy)-3-pentylphenyl]carbamate.

EXAMPLE 38

PREPARATION OF N-[4-(3-PENTYLPHENOXY)-2,3,5,6-TETRAPEN-TYL]-N'-(2,2-DIMETHOXYETHYL)-N-METHYLUREA

[4-(3-Pentylphenoxy)-3-pentylphenyl]carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4-(3-pentylphenoxy)-3-pentylphenyl]-N'-(2,2-dimethoxyethyl)-N'-methylurea.

EXAMPLE 39

PREPARATION OF 1-METHYL-3-[4-(3-PENTYLPHENOXY)-2,3,5,6-TETRAPENTYL]-4-IMIDAZOLIN-2-ONE

N-[4-(3-Pentylphenoxy)-2,3,5,6-tetrapentyl]-N-(2,2-dimethoxyethyl)-N'-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes and then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3-[4-(3-pentylphenoxy)-2,3,5,6-tetrapentyl]-4-imidazolin-2-one.

EXAMPLE 40

PREPARATION OF ethyl [4-[3-(TRICHLOROMETHYL)PHENOXY]-3-(TRICHLOROMETHYL)PHENYL]CARBAMATE.

4-[3-(Trichloromethyl)phenoxy]-3-(trichloromethyl)-benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-[3-(trichloromethyl)phenoxy]-3-(trichloromethyl)phenyl]carbamate.

EXAMPLE 41

PREPARATION OF N-[4-[3-(TRICHLOROMETHYL)PHENOXY]3-3(TRICHLOROMETHYL)PHENYL]-N-(2,2-DIMETHOXYETHYL)-N-METHYLUREA

Ethyl [4-[3-Trichloromethyl)phenoxy]-3-(trichloromethyl)phenyl]carbamate (0.1 mole) and toluene (100 ml) are charged into a glass reaction vessel fitted with a mechanical stirrer, thermometer and condenser. N-(2,2-dimethoxyethyl) methanamine (0.15 mole) is added to the vessel and the mixture is refluxed for 16 hours. Solvent is then removed by mild warming under reduced pressure to yield the desired product N-[4-[3-(trichloromethyl)phenoxy]-3- (trichloromethyl) phenyl]-N'-(2,2-dimethoxyethyl)-N'-methylurea.

EXAMPLE 42

PREPARATION OF 1-METHYL-3-[4-[3-(TRICHLOROMETHYL)-PHENOXY]-3-(TRICHLOROMETHYL)PHENYL]-4-IMIDAZOLIN-2-ONE

N-[4-[3-(Trichloromethyl)phenoxy]-3-(trichloromethyl) phenyl]-N-(2,2-dimethoxyethyl)-N'-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes and then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3[4-[3-(trichloromethyl)phenoxy]-3-(trichloromethyl)phenyl]-4-imidazolin-2-one.

EXAMPLE 43

PREPARATION OF ETHYL [4-[3,5-(DICYANOPHENYL)THIO]PHENYL]CARBAMATE

4-[3,5-(Dicyanophenyl)thio]benzenamine (0.01 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-[3,5-(dicyanophenyl)thio]phenyl]carbamate.

EXAMPLE 44

PREPARATION OF N-[4-[3,5-(DICYANOPHENYL)THIO]PHENYL]-N'- (2,2-DIMETHOXYETHYL)-N'-METHYLUREA

Ethyl [4-[3,5-(dicyanophenyl)thio]phenyl]carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4-3,5-(dicyanophenyl)thio]phenyl]-N'-(2,2-dimethoxyethyl)-N'-methylurea.

EXAMPLE 45

PREPARATION OF 1-METHYL-3-[4-[3,5-(DICYANOPHENYL)THIO]-PHENYL]4-IMIDAZOLIN-2-ONE

N-4-[3,5-(Dicyanophenyl)thio]phenyl]-N'-(2,2-dimethoxyehtyl)-N'-methylurea (0.02 mole), water (30 ml) and concentrated hydrochloric acid (3 ml) are charged into a glass reaction vessel fitted with a mechanical stirrer thermometer and condenser. The mixture is refluxed for a period of about 30 minutes and then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3-[4-[3,5-(dicyanophenyl) thio]phenyl]-4-imidazolin-2-one.

EXAMPLE 46

PREPARATION OF ETHYL [4-(PHENYLSULFINYL)-3-BUTOXYPHENYL]-CARBAMATE 4-(Phenylsulfinyl)-3-butoxybenzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-(phenylsulfinyl)-3-butoxyphenyl]carbamate.

EXAMPLE 47

PREPARATION OF N-[4-(PHENYLSULFINYL)-3-BUTOXYPHENYL]-N'- (2,2-DIMETHOXYETHYL)-N'-METHYLUREA

Ethyl [4-(phenylsulfinyl)-3-butoxyphenyl]carbamate (0.1 mole and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4-phenylsulfinyl)-3-butoxyphenyl]-N'-(2,2-dimethoxyethyl-N'-methylurea.

EXAMPLE 48

PREPARATION OF
1-METHYL-3-[4-(PHENYLSULFINYL)-3-BUTOXY-PHENYL]-4-IMIDAZOLIN-2-ONE

N-[4-(Phenylsulfinyl)-3-butoxyphenyl]-N'-(2,2-dimethoxyethyl)-N'-methylurea(0.02 mole), water (30 ml) and concentrated hydrochloric acid (3 ml) are charged into a glass reaction vessel fitted with a mechanical stirrer, thermometer and condenser. The mixture is refluxed for a period of about 30 minutes and then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3-[4-(phenylsulfinyl)-3-butoxyphenyl]-4-imidazolin-2-one.

EXAMPLE 49

PREPARATION OF ETHYL [4-[[3,5-BIS(ETHYLTHIO)PHENYL]SULFONYL]-PHENYL]CARBAMATE

4-[[3,5-Bis(ethylthio)phenyl]sulfonyl]benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-[3,5-bis(ethylthio)phenyl]sulfonyl]phenyl]carbamate.

EXAMPLE 50

PREPARATION OF N-[4-[[3,5-BIS(ETHYLTHIO)PHENYL]SULFONYL]PHENYL]-N'-(2,2,-DIEMTHOXYETHYL)-N'-METHYLUREA

Ethyl [4-[[3,5-Bis(ethylthio)phenyl]sulfonyl]phenyl]carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4-[[3,5-bis(ethylthio)phenyl]sulfonyl]phenyl]-N-(2,2-dimethoxyethyl)-N-methylurea.

EXAMPLE 51

PREPARATION OF 1-METHYL-3-[4-[[3,5-BIS(ETHYLTHIO)PHENYL]-SULFONYL]PHENYL]-4-IMIDAZOLIN-2-ONE

N-[4-[[3,5-Bis(ethylthio)phenyl]sulfonyl]phenyl]-N-(2,2-dimethoxyethyl)-N-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minute then cooled and extracted with ethyl acetate. The extract is washed with dilute aqueous sodium bicarbonate, with two portions of water and is then dried. The ethyl acetate is removed by mild warning under reduced pressure to yield the desired product 1-methyl-3-[4-[[3,5-bis-(ethylthio)phenyl]sulfonyl]phenyl]-4-imidazolin-2-one.

EXAMPLE 52

PREPARATION OF ETHYL [4-(3,5-DICYANOPHENOXY)-3,5-DICYANO-PHENYL]CARBAMATE 4-(3,5-Dicyanophenoxy)benzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-(3,5-dicyanophenoxy)-3,5-dicyanophenyl]carbamate.

EXAMPLE 53

PREPARATION OF N-[4-(3,5-DICYANOPHENOXY)-3,5-DICYANO-PHENYL]-N'-(2,2-DIMETHOXYETHYL)-N'-METHYLUREA.

Ethyl [4-(3,5-dicyanophenoxy)-3,5-dicyanophenyl]carbamate (0.1 mole) and toluene (100 ml) are charged into a glass reaction vessel fitted with a mechanical stirer, thermometer and condenser. N-(2,2-dimethoxyethyl)methamine (0.15 mole) is added to the vessel and the mixture is refluxed for 16 hours. Solvent is then removed by mild warming under reduced pressure to yield the desired product N-[4-(3,5-dicyanophenoxy)-3,5-dicyanophenyl](2,2-dimethoxyethyl)-N'-methylurea.

EXAMPLE 54

PREPARATION OF 1-METHYL-3-[4-(3,5-DICYANOPHENOXY)-3,5-DICYANOPHENYL]-4-IMIDAZOLIN-2-ONE

N-[4-(3,5-Dicyanophenoxy)-3,5-dicyanophenyl]-N'-(2,2-dimethoxyethyl)-N'-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes then cooled and extracted with ethyl acetate. The extract is washed with dilute aqueous sodium bicarbonate, with two portion of water and is then dried. The ethyl acetate is removed by mild warming under reduced pressure to yield the desired product 1-methyl-3-[4-(3,5-dicyanophenoxy)3,5-dicyanophenyl]-4-imidazolin-2-one.

EXAMPLE 55

PREPARATION OF ETHYL [4-(4-NITROPHENOXY)-3-NITROPHENYL]CARBAMATE 4-(4-Nitrophenoxy)-3-nitrobenzenamine (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed with 2 portions of water (50 ml), dried and the solvent is then removed to yield the desired product ethyl [4-(4-nitrophenoxy)-3-nitrophenyl]carbamate.

EXAMPLE 56

PREPARATION OF N-[4-(4-NITROPHENOXY)-3-NITROPHENYL]-N'-(2,2-DIMETHOXYETHYL)-N'-METHYLUREA

Ethyl [4-(4-nitrophenoxy)-3-nitrophenyl]carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4-(4-nitrophenoxy)-3-nitrophenyl]-N'-(2,2-dimethoxyethyl)-N'-methylurea.

EXAMPLE 57

PREPARATION OF 1-METHYL-3-[4-(4-NITROPHENOXY)-3-NITROPHENYL]-4-IMIDAZOLIN-2-ONE

N-[4-(4-Nitrophenoxy)-3-nitrophenyl]-N'-(2,2-dimethoxyethyl)-N'-methylurea (0.02 mole), water (30 ml) and concentrated hydrochloric acid (3 ml) are charged into a glass reaction vessel fitted with a mechanical stirrer, thermometer and condenser. The mixture is refluxed for a period of about 30 minutes then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3-[4-(4-nitrophenoxy)-3-nitrophenyl]-4-imidazolin-2-one.

EXAMPLE 58

PREPARATION OF ETHYL [4-(3,4-DICHLOROPHENOXY)-3-(ETHYLTHIO)PHENYL]CARBAMATE 4-(3,4-Dichlorophenoxy)-3-(ethylthio)benzenamine, (0.1 mole) and pyridine (50 ml) are charged into a glass reaction vessel fitted with a mechanical stirrer and thermometer and are cooled to about 5° C. Ethyl chloroformate (0.125 mole) is added, with stirring, at about 5° C. Stirring is continued for a period of about 30 minutes at about 5° C., then for an additional 16 hours at room temperature. The mixture is then washed in 2 portions of water (50 ml), dried and the solvent is then removed to yield the desired product ethyl [4-(3,4-dichlorophenoxy)-3-(ethylthio)phenyl]carbamate.

EXAMPLE 59

PREPARATION OF N-[4-(3,4-DICHLOROPHENOXY)-3-(ETHYLTHIO)PHENYL]-N-(2,2-DIMETHOXYETHYL)-N-METHYLUREA

Ethyl [4-(3,4-dichlorophenoxy)-3-(ethylthio)phenyl]carbamate (0.1 mole) and toluene (100 ml) are charged into a glass reaction vessel fitted with a mechanical stirrer, thermometer and condenser. N-(2,2-dimethoxyethyl)methanamine (0.15 mole) is added to the vessel and the mixture is refluxed for 16 hours. Solvent is then removed by mild warming under reduced pressure to yield the desired product N-[4-(3,4-dichlorophenoxy)-3-(ethylthio)phenyl]-N'-(2,2-dimethoxyethyl)-N'-methylurea.

EXAMPLE 60

PREPARATION OF 1-METHYL-3-[4-(3,4-DICHLOROPHENOXY)-3-(ETHYLTHIO)PHENYL]-4-IMIDAZOLIN-2-ONE

N-[4-(3,4-Dichlorophenoxy)-3-(ethylthio)phenyl]-N'-(2,2-dimethoxyethyl)-N'-methylurea (0.02 mole), water (30 ml) and concentrated hydrochloric acid (3 ml) are charged into a glass reaction vessel fitted with a mechanical stirrer, theremometer and condenser. The mixture is refluxed for a period of about 30 minutes then cooled and extracted with ethyl acetate. The extract is washed with dilute aqueous sodium bicarbonate, with two portions of water and is then dried. The ethyl acetate is removed by mild warming under reduced pressure to yield the desired product 1-methyl-3-[4-(3,4-dichlorophenoxy)-3-(ethylthio)phenyl]-4-imidazolin-2-one.

Additional compounds within the scope of this invention which can be prepared by the procedures of the foregoing example are 1-methyl-3-[4-(3-methoxyphenoxy)-3-ethoxyphenyl]-4-imidazolin-2-one; 1-methyl-3-[4-(3,4,5-tripentylphenoxy)phenyl]-4-imidazolin-2-one; 1-methyl-3-[4-(3,6-dichlorophenoxy)-3,5-dimethoxyphenyl]-4-imidazolin-2-one; 1-methyl-3-[4-(3-(trifluoromethyl)phenoxy]-3-(trifluoromethyl)phenyl]-4-imidazolin-2-one; 1-methyl-2-[4-(3,4,5-tribromophenoxy)-3,5-dibromophenyl]-4-imidazolin-2-one; 1-methyl-3-[4-(4-bromophenoxy)-3-butylphenyl]-4-imidazolin-2-one; 1-methyl-3-[4-(phenylmethyl)-3-(chloromethyl)phenyl]-4-imidazolin-2-one; 1-methyl-3-[4-[[4-(methylthio)phenyl]methyl]-3-bromophenyl]-4-imidazolin-2-one; 1-methyl-3-[4-[(3,5-dipropylphenyl)methyl]phenyl-4-imidazolin-2-one; 1-methyl-3-[4-[(3-chloro-5-methylphenyl)methyl]-3-methyl-5-chlorophenyl]-4-imidazolin-2-one; 1-methyl-3-[4-[[3,4-bis(trichloromethyl)phenyl]methyl]-2-chlorophenyl]-4-imidazolin-2-one; 1-methyl-3-[4-[[4-trifluoromethyl)phenyl]thio]-phenyl]-4-imidazolin-2-one; 1-methyl-3-[4-[(3-methoxyphenyl)thio]-3-methoxyphenyl]-4-imidazolin-2-one; 1-methyl-3-[4-[(3,5-dibutylphenyl)thio]-3-methoxyphenyl]-4-imidazolin-2-one; 1-methyl-3-[4-[3-(chlorophenyl)-sulfinyl]-3-chlorophenyl]-4-imidazolin-2-one; 1-methyl-3-[4-(phenylsulfinyl)-3-(chloromethylphenyl]-4-imidazolin-2-one; 1-methyl-3-[4-[(2,3,5,6-tetrachlorophenyl)sulfinyl]]-4-imidazolin-2-one; 1-methyl-3-[4-[3,4,5-(trichlorophenyl)sulfonyl]-3-bromophenyl]-4-imidazolin-2-one; 1-methyl-3-[4-[3-(2,2,2-trichloroethyl)phenoxy]phenyl]-4-imidazolin-2-one; 1-methyl-3-[4-[(3-bromophenyl)sulfonyl]-3,4,5-trichlorophenyl]-imidazolin-2-one; 1-methyl-3-[4-(4-cyanophenoxy)-phenyl]-4-imidazolin-2-one; 1-methyl-3-[4-(2,6-dinitrophenoxy)phenyl]-4-imidazolin-2-one; 1-methyl-3-[4-(3-cyanophenoxy)-3-cyanophenyl]-4-imidazolin-2-one; 1-methyl-3-[4-[(2-chlorophenyl) sulfonyl]-2-nitrophenyl]-4-imidazolin-2-one; 1-methyl-3-[4-phenoxy-3(ethylthio)phenyl]-4-imidazolin-2-one; 1-methyl-3-[4-[(2,6-dichloro-3,5-dimethoxy)phenoxy]-2,6-dimethyl-3,5-dichlorophenyl]-4-imidazolin-2-one.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates which comprise an active compound according to this invention and as the inert carrier a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 61

Preparation of a Dust

Product of Example 3: 10
Powdered Talc: 90

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and the plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB,) 2,4,-DEB, 4-CPB, 4-CPA, 4-CPP, 2,4,5-TB, 2,4,5-TES, 3,4-DA, silvex and the like; carbamate herbicides such as IPC, CIPC, swep barban, BCPC, CEPC, CPPC, and the like; thiocarbamate and dithiocarbamate herbicides such as CDEC, metham sodium, EPTC, diallate, PEBC, perbulate, vernolate and the like, substituted urea herbicides such as norea, siduron, dichloral urea, chloroxurn, cyculron, fenuron, monuron, monuron TCA, diuron, linuron, monlinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne and the like; chloracetamide herbicides such as 4-(chloroacetyl)morpholine, 1-(chloroacetyl)-piperidine and the like; chlorinated aliphtic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3, 6-dichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS bromacil, 2-(3,4-dichlorophenyl)-4-methyl-1,2,4-oxadiazolidine, 3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field penny-cress, ryegrass, goose grass, chickweed, wild oats, velvet-leaf, purslane, barnyard-grass, smartweed, knotweed, cocklebur, wild buckwheat, kochia, medic, corn cockle, ragweed, sow-thistle, coffeeweed, croton, cuphea, dodder, fumitory, groundsel, hemp nettle, knawel, spurge, spurry, emex, jungle rice, pondweed, dog gennel, carpetweed, morningglory, bedstraw, duchsalad, naiad, cheatgrass, fall panicum, kimsonweed, witchgrass, switch-grass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toad-flax, yarrow, aster, gromwell, horsetail, ironweed, sesbania, bulrush, cattail and winter-cress.

Similary, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively non-toxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as per- and post-emergence testing.

The herbicidal activity of the compounds of this invention can be demonstrated by experiments carried out for the pre-emergence control of a variety of weeds. In these experiments small plastic greenhouse pots filled with dry soil are seeded with the various weed seeds. Twenty-four hours or less after seeding the pots are sprayed with water until the soil is wet and a test compound formulated as an aqueous emulsions of acetone solutions containing emulsifiers were sprayed at the indicated concentrations on the surface of the soil.

After spraying, the soil containers are placed in the greenhouse and provided with supplementary heat as required and daily or more frequent watering. The plants are maintained under these conditions for a period of from 15 to 21 days, at which time the condition of the plants and the degree of injury to the plants is rated on a scale of from 0 to 10, as follows: 0=no injury, 1,2=slight injury, 3,4=moderate injury, 5,6=moderately severe injury, 7,8,9=severe injury, 10—death and N.E.—no emergence of the plant. The effectiveness of these compounds is demonstrated by the data in Tables 1 and 3.

The herbicidal activity of the compounds of this invention can also be demonstrated by experiments carried out for the post-emergence control of a variety of weeds. In these experiments the compounds to be tested are formulated as aqueous emulsions and sprayed at the desired dosage on the foliage of the weeds that have attained a prescribed size. After spraying the plants are placed in a greenhouse and watered daily or more frequently. Water is not applied to the foliage of the treated plants. The severity of the injury is determined 14 days after treatment and is rated on the scale of from 0 to 10 heretofore described. The effectiveness of these compounds is demonstrated by the data in Tables 2 and 4.

The abbreviations used for weed species in the tables are:

| Weed Species | Abbreviation |
|---|---|
| Yellow Nutsedge | YNSG |
| Wild Oats | WOAT |
| Jimsonweed | JMWD |
| Velvetleaf | VTLF |
| Johnsongrass | JNGS |
| Pigweed | PIGW |
| Wildmustard | WMSTD |
| Yellow Foxtail | YFLX |
| Barnyardgrass | BNGS |
| Crabgrass | CBGS |
| Cheatgrass | CTGS |
| Wild Morningglory | MNGY |
| Bindweed | BDWD |
| Soybean | SOYB |

TABLE 1

INJURY RATING

| WEED SPECIES | YNSG | WOAT | JMWD | VTLF | JNGS | PIGW | WMSTD | YFLX | BNGS | CBGS | CTGS | MNGY |
|---|---|---|---|---|---|---|---|---|---|---|---|---|
| Compound of example 3 | | | | | | | | | | | | |
| 14 days after treatment: | | | | | | | | | | | | |
| application rate, lbs./acre | | | | | | | | | | | | |
| #/A | | | | | | | | | | | | |
| 8 | 0 | 4 | 10 | 10 | 2 | 4 | 10 | 7 | 7 | 9 | 7 | 8 |
| 2 | 0 | 0 | 5 | 4 | 0 | 0 | 10 | 0 | 2 | 7 | 3 | 0 |
| 1 | 0 | 0 | 3 | 1 | 0 | 1 | 10 | 0 | 2 | 2 | 4 | 0 |
| 21 days after treatment: | | | | | | | | | | | | |
| application rate, lbs./acre | | | | | | | | | | | | |
| 8 | 0 | 4 | 10 | 10 | 5 | 9 | 10 | 8 | 10 | 9 | 10 | 10 |
| 2 | 0 | 0 | 10 | 5 | 0 | 0 | 10 | 0 | 2 | 3 | 0 | 0 |
| 1 | 0 | 0 | 5 | 0 | 0 | 2 | 10 | 0 | 2 | 0 | 0 | 0 |

TABLE 2

| WEED SPECIES | YNSG | WOAT | JMWD | JNGS | PIGW | WMSTD | YFLX | BNGS | CBGS | MNGY | BDWD | SOYB |
|---|---|---|---|---|---|---|---|---|---|---|---|---|
| INJURY RATING | | | | | | | | | | | | |
| Compound of example 3 14 days after treatment: application rate, lbs./acre #/A | | | | | | | | | | | | |
| 2 | 0 | 2 | 7 | 0 | 4 | 10 | 3 | 2 | 3 | 9 | 3 | 3 |
| 1 | 0 | 2 | 10 | 0 | 1 | 2 | 0 | 0 | 0 | 8 | 0 | 0 |
| 0.5 | 0 | 0 | 3 | 0 | 0 | 0 | 0 | 0 | 0 | 0 | 0 | 3 |

TABLE 3

| WEED SPECIES | YNSG | WOAT | JMWD | VTLF | JNGS | PIGW | WMSTD | YFLX | BNGS | CBGS | CTGS | MNGY |
|---|---|---|---|---|---|---|---|---|---|---|---|---|
| INJURY RATING | | | | | | | | | | | | |
| Compound of Example 3 14 days after treatment: application rate, lbs./acre #/A | | | | | | | | | | | | |
| 8 | 0 | 3 | 0 | 3 | 0 | 8 | 10 | 6 | 3 | 6 | 9 | 8 |
| 21 days after treatment: application rate, lbs./acre | | | | | | | | | | | | |
| 8 | 1 | 5 | 10 | 3 | 3 | 9 | 10 | 9 | 4 | 5 | 0 | 10 |

TABLE 4

| WEED SPECIES | YNSG | WOAT | JMWD | JNGS | PIGW | WMSTD | YFLX | BNGS | CBGS | MNGY | BDWD | SOYB |
|---|---|---|---|---|---|---|---|---|---|---|---|---|
| INJURY RATING | | | | | | | | | | | | |
| Compound of Example 3 14 days after treatment: application rate, lbs. acre #/A | | | | | | | | | | | | |
| 4 | 1 | 6 | 10 | 7 | 10 | 10 | 10 | 7 | 10 | 10 | 10 | 3 |
| 2 | 0 | 8 | 10 | 7 | 10 | 10 | 10 | 10 | 10 | 10 | 9 | 3 |
| 1 | 0 | 3 | 10 | 5 | 10 | 10 | 10 | 10 | 10 | 10 | 8 | 2 |

I claim:

1. A compound of the formula

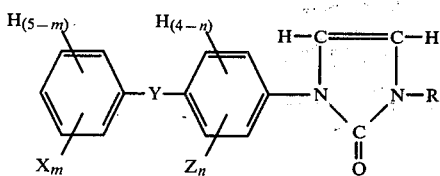

wherein X and Z are each independently selected from the group consisting of halogen, trihalo loweralkyl, nitro, cyano, loweralkyl, loweralkoxy and loweralkylthio; m and n are each independently integers of from 0 to 4; Y is selected from the group consisting of oxygen, sulfur, methylene, sulfonyl and sulfinyl; and R is selected from the group consisting of hydrogen and alkyl.

2. The compound of claim 1, 1-methyl-3-(4-phenoxyphenyl)-4-imidazolin-2-one.

3. The compound of claim 1, 1-methyl-3-[4-(3-methoxy-4-chlorophenoxy)phenyl]-4-imidazolin-2-one.

4. The compound of claim 1, 1-methyl-3-[4-(3-chloro-4-methylphenoxy)phenyl]-4-imidazolin-2-one.

5. The compound of claim 1, 1-methyl-3-[4-(3,4-dichlorophenoxy)phenyl]-4-imidazolin-2-one.

6. The compound of claim 1, 1-methyl-3-[3,5-dichloro-4-(3,5-dichlorophenoxy)phenyl]-4-imidazolin-2-one.

7. The compound of claim 1, 1-methyl-3-(3,5-dinitro-4-phenoxyphenyl)-4-imidazolin-2-one.

8. The compound of claim 1, 1-methyl-3-[4-[3(trifluoromethyl)phenoxy]phenyl]-4-imidazolin-2-one.

9. A herbicidal composition comprising an inert carrier and as an essential active ingredient, in a quantity toxic to weeds, a compound of claim 1.

10. A method of controlling weeds which comprises contacting said weeds with a herbicidally effective quantity of the composition of claim 9.